United States Patent [19]

Seybold et al.

[11] Patent Number: 4,473,391
[45] Date of Patent: Sep. 25, 1984

[54] HERBICIDES CONTAINING THIAZOLO[2,3-b]QUINAZOLONES AS ACTIVE INGREDIENTS, AND THEIR USE FOR REGULATING PLANT GROWTH

[75] Inventors: Guenther Seybold, Neuhofen; Bruno Wuerzer, Otterstadt, both of Fed. Rep. of Germany

[73] Assignee: BASF Aktiengesellschaft, Fed. Rep. of Germany

[21] Appl. No.: 435,367

[22] Filed: Oct. 20, 1982

[30] Foreign Application Priority Data

Oct. 28, 1981 [DE] Fed. Rep. of Germany ....... 3142728

[51] Int. Cl.³ ...................... A01N 43/78; A01N 43/54
[52] U.S. Cl. ......................................................... 71/90
[58] Field of Search ............................................ 71/90

[56] References Cited

U.S. PATENT DOCUMENTS 2,594,381 4/1952 Bober ................................. 71/90 X

FOREIGN PATENT DOCUMENTS 2557425 6/1977 Fed. Rep. of Germany .
54-5995 7/1979 Japan .

OTHER PUBLICATIONS

J. Sci. Ind. Research (1958), pp. 120–123.

*Primary Examiner*—Catherine L. Mills
*Attorney, Agent, or Firm*—Keil & Weinkauf

[57] ABSTRACT

Herbicides which contain thiazolo[2,3-b]-quinazolones of the formula

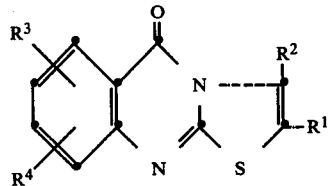

where $R^1$, $R^2$, $R^3$ and $R^4$ have the meanings given in the description, are used to regulate plant growth, and control undesired growth.

4 Claims, No Drawings

HERBICIDES CONTAINING THIAZOLO[2,3-b]QUINAZOLONES AS ACTIVE INGREDIENTS, AND THEIR USE FOR REGULATING PLANT GROWTH

The present invention relates to herbicides and agents for regulating plant growth, which contain thiazolo[2,3-b]quinazolones as active ingredients, and to processes for regulating and controlling plant growth with such herbicides.

Thiazolo[2,3-b]quinazolones having an antibacterial and pharmaceutical action have been disclosed (J. Sci. Ind. Research 17 B (1958), 120–123; German Laid-Open Application DOS 2,557,425).

We have found that herbicidal agents which contain thiazolo[2,3-b]quinazolones of the formula

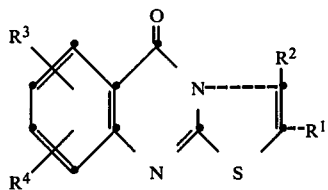

where $R^1$ and $R^2$ independently of one another are hydrogen, halogen, nitro, cyano, alkyl, haloalkyl, cycloalkyl, alkoxy, alkylthio, thiophenyl, amino, alkylamino, dialkylamino, aminoalkyl, alkylaminoalkyl, dialkylaminoalkyl, alkanoylamino, haloalkanoylamino, carboxyl, carbamyl, dialkylcarbamido, alkoxycarbonyl, alkoxycarbonylalkyl, unsubstituted or alkoxy-substituted alkoxycarbonyl, sulfo, sulfino, alkylsulfonyl, alkylsulfinyl, chlorosulfonyl, phenylsulfonyl, sulfamyl, alkylaminosulfinyl, alkylaminosulfonyl, hydroxyalkylaminosulfonyl, dihydroxyalkylaminosulfonyl, dihydroxyalkylaminosulfonyl, morpholinylsulfonyl, alkylsulfonylamino, alkoxycarbonylalkylamino, unsubstituted or halogen-, alkoxy- or carboxyalkoxy-substituted phenyl, or unsubstituted or halogen- or alkyl-substituted hetaryl and $R^3$ and $R^4$ independently of one another are hydrogen, halogen, nitro, cyano, alkyl, haloalkyl, cycloalkyl, alkoxy, alkylthio, thiophenyl, amino, alkylamino, dialkylamino, aminoalkyl, alkylaminoalkyl, dialkylaminoalkyl, alkanoylamino, haloalkanoylamino, carboxyl, carbamyl, dialkylcarbamido, alkoxycarbonyl, alkoxycarbonylalkyl, unsubstituted or alkoxy-substituted alkoxycarbonyl, sulfo, sulfino, alkylsulfonyl, alkylsulfinyl, chlorosulfonyl, phenylsulfonyl, sulfamyl, alkylaminosulfinyl, alkylaminosulfonyl, hydroxyalkylaminosulfonyl, dihydroxyalkylaminosulfonyl, dihydroxyalkylaminosulfonyl, morpholinylsulfonyl, alkylsulfonylamino, alkoxycarbonylalkylamino, unsubstituted or halogen-, alkoxy- or carboxyalkoxy-substituted phenyl or unsubstituted or halogen- or alkyl-substituted hetaryl, or their acid addition salts are very active and have growth-regulating properties.

The substituents $R^1$, $R^2$, $R^3$ and $R^4$ in formula I are hydrogen, halogen, eg. fluorine, chlorine, bromine or iodine, nitro, cyano, alkyl of 1 to 12, preferably 1 to 4, carbon atoms, eg. methyl, ethyl, n-propyl, isopropyl, n-butyl, i-butyl, sec.-butyl or tert.-butyl, haloalkyl of 1 to 4 carbon atoms, eg. chloromethyl, fluoromethyl, difluoromethyl, trichloromethyl, trifluoromethyl, pentafluoroethyl, 2-chloro-1,1,2,2-tetrafluoroethyl or nonafluoro-n-butyl, cycloalkyl of 3 to 6 carbon atoms, eg. cyclopropyl, cyclopentyl or cyclohexyl, alkoxy or alkylthio of 1 to 4 carbon atoms, eg. methoxy, methylthio, ethylthio, n-propylthio, ethoxy, n-butoxy, n-butylthio, isopropoxy or tert.-butoxy, thiophenyl, amino, alkylamino or dialkylamino, where alkyl is of 1 to 4 carbon atoms, eg. methylamino, dimethylamino, n-butylamino, diethylamino, isopropylamino or methylethylamino, aminoalkyl, alkylaminoalkyl or dialkylaminoalkyl, where alkyl is in each case of 1 to 4 carbon atoms, eg. aminomethyl, methylaminomethyl, dimethylaminomethyl, aminoethyl, methylaminoethyl or dimethylaminoethyl, alkanoylamino or haloalkanoylamino of 2 to 5 carbon atoms, eg. acetylamino, chloroacetylamino, trifluoroacetylamino, propionylamino or 2-chloropropionylamino, carboxyl, carbamyl, dialkylcarbamido, where alkyl is of 1 to 4 carbon atoms, eg. N,N-dimethylcarbamido, N,N-diethylcarbamido or N,N-di-n-butylcarbamido, alkoxycarbonyl of 2 to 5 carbon atoms, eg. methoxycarbonyl, ethoxycarbonyl, n-propoxycarbonyl, tert.-butoxycarbonyl or isobutoxycarbonyl, alkoxycarbonylalkyl of 3 to 6 carbon atoms, eg. methoxycarbonylmethyl, ethoxycarbonylmethyl or n-butoxycarbonylmethyl, unsubstituted or alkoxy-substituted alkoxycarbonyl of 2 to 6 carbon atoms, eg. methoxycarbonyl, ethoxycarbonyl, n-propoxycarbonyl, n-butoxycarbonyl, isopropoxycarbonyl, 2-methoxyethoxycarbonyl, ethoxymethoxycarbonyl or 2-ethoxyethoxycarbonyl, sulfo, sulfino, alkylsulfonyl or alkylsulfinyl of 1 to 4 carbon atoms, eg. methylsulfonyl, methylsulfinyl, isopropylsulfonyl, n-propylsulfinyl, n-butylsulfonyl, n-butylsulfinyl, chlorosulfonyl, phenylsulfonyl, sulfamyl, alkylaminosulfonyl or alkylaminosulfinyl of 1 to 4 carbon atoms, eg. methylaminosulfonyl, methylaminosulfinyl, isopropylaminosulfonyl, n-butylaminosulfonyl or n-butylaminosulfinyl, hydroxyalkylaminosulfonyl or dihydroxyalkylaminosulfonyl, where hydroxyalkyl is of 1 to 4 carbon atoms, eg. 2-hydroxyethylaminosulfonyl or di-(2-hydroxyethyl)-aminosulfonyl, alkylsulfonylamino of 1 to 4 carbon atoms, eg. methylsulfonylamino, isopropylsulfonylamino or isobutylsulfonylamino, alkoxycarbonylalkylamino of 3 to 6 carbon atoms, eg. 2-methoxycarbonylethylamino or 2-n-butoxycarbonylethylamino, unsubstituted, halogen-substituted, or alkoxy- or carboxyalkoxy-substituted (the substituent in each case being of up to 5 carbon atoms) phenyl, eg. phenyl, 4-chlorophenyl, 4-methoxyphenyl, 4-carboxymethoxyphenyl, 4-(2-carboxyethoxy)-phenyl or 3,5-dichlorophenyl, or unsubstituted, halogen-substituted or alkyl-substituted (alkyl being of up to 4 carbon atoms) hetaryl, eg. thien-2-yl, thiazol-2-yl, fur-2-yl, benzimidazol-2-yl, 2-chloro-thien-4-yl, 2-methylthien-4-yl or 1-methyl-benzimidazol-yl.

Preferred compounds of the formula I are those where $R^1$ and $R^2$, independently of one another, are hydrogen, alkyl or haloalkyl each of 1 to 4 carbon atoms, aminoalkyl, alkylaminoalkyl or dialkylaminoalkyl, alkyl in each case being of 1 to 4 carbon atoms, alkoxycarbonyl of 2 to 5 carbon atoms or phenyl which is unsubstituted or substituted by chlorine, fluorine, alkoxy of 1 to 4 carbon atoms or alkoxycarbonyl of 2 to 5 carbon atoms, and $R^3$ and $R^4$ independently of one another are hydrogen, halogen, cyano, alkoxy of 1 to 4 carbon atoms, carboxyl, carbamyl or alkoxycarbonyl of 2 to 5 carbon atoms, as well as those where $R^1$ and $R^2$ independently of one another are hydrogen, methyl, ethyl, bromomethyl, dialkylaminomethyl, alkyl being of 1 to 4 carbon atoms, alkoxycarbonyl of 2 to 5 carbon atoms or phenyl which is unsubstituted or substituted by chlorine, fluorine or alkoxy of 1 to 4 carbon atoms and $R^3$ and $R^4$ independently of one another are hydrogen, chlorine, bromine, cyano, methoxy, carboxyl, carbamyl or alkoxycarbonyl of 2 to 5 carbon atoms, or those where $R^1$ is hydrogen, methyl, ethyl or bromomethyl, $R^2$ is hydrogen, methyl or ethyl and $R^3$ and $R^4$ independently of one another are hydrogen, chlorine or bromine, or acid addition salts of these compounds. In the last-mentioned compounds, if $R^3$ and $R^4$ are chlorine or bromine, these substituents are preferably in the 7- and/or 9-position.

Particularly preferred compounds are 3-methyl-thiazolo[2,3-b]-quinazolones which are unsubstituted or methyl-substituted in the 2-position, and acid addition salts of these compounds.

The thiazolo[2,3-b]-quinazolones of the formula I are obtained by reacting an anthranilic acid derivative of the formula

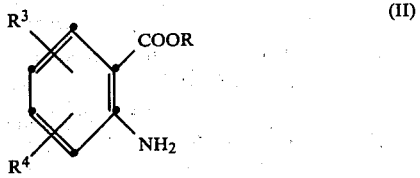

where R is hydrogen or alkyl, preferably of 1 to 4 carbon atoms, and $R^3$ and $R^4$ have the above meanings, with a thiocyanate derivative of the formula

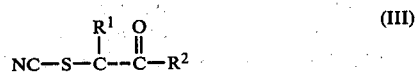

where $R^1$ and $R^2$ have the above meanings, or with a thiazole derivative of the formula

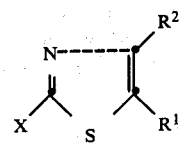

where X is fluorine, chlorine, bromine, alkylsulfonyl or arylsulfonyl and $R^1$ and $R^2$ have the above meanings.

The condensation of the anthranilic acid derivative of the formula II with the thiocyanate derivative of the formula III is preferably carried out in an aqueous medium in the presence of a strong mineral acid, such as hydrogen chloride, hydrogen bromide or sulfuric acid. The starting materials are preferably employed in approximately the stoichiometric ratio; an excess of one or other reactant does not interfere with the course of the reaction. The reaction temperature may be varied from 40° to 150° C., preferably from 60° to 100° C. The amount of acid used is from 1 to 2 mole equivalents per mole of the anthranilic acid derivative of the formula II.

The reaction of the anthranilic acid derivative of the formula II with the thiazole derivative of the formula IV is carried out at from 100° to 200° C., preferably from 130° to 160° C. Again, the reactants are employed in approximately the stoichiometric ratio. Addition of acid is not necessary. The reaction may, if desired, be carried out in the presence of a solvent, for example a halohydrocarbon, eg. dichlorobenzene or trichlorobenzene, a polyhydric alcohol, eg. glycol, ethylglycol, butylglycol or diethylene glycol, an ester, eg. methylglycol acetate, or dimethylformamide. Mixtures of these solvents may also be used. Preferably the reaction is carried out in the absence of a solvent. X in formula IV is preferably chlorine.

Some of the anthranilic acid derivatives of the formula II, thiocyanate derivatives of the formula III and thiazole derivatives of the formula IV, used as starting materials, have previously been disclosed; the compounds of these categories can be prepared by analogy to conventional methods (J. Amer. Chem. Soc. 74 (1952), 1719; Proc. Ind. Acad. Sci. 22A (1945), 343).

The acid addition salts of the thiazolo[2,3-b]-quinazolones of the formula I are obtained by protonation with the appropriate acids in the presence of an inert solvent, such as tetrahydrofuran, dioxane, tert.-butyl methyl ether, methylene chloride or acetonitrile.

The acids which may be used to form the corresponding salts include inorganic acids, eg. hydrochloric acid, hydrobromic acid, hydrofluoric acid, sulfuric acid, phosphoric acid and perchloric acid, and organic acids, eg. monochloroacetic acid, dichloroacetic acid, trichloroacetic acid and trifluoroacetic acid.

EXAMPLE 389 parts of anthranilic acid were introduced into 3,000 parts of 5% strength hydrochloric acid. 320 parts of acetylmethyl thioacetate were added dropwise over one hour at 80° C., the mixture was refluxed for 3 hours and the product was filtered off cold. 422 parts of 3-methyl-5H-thiazolo[2,3-b]-quinazolin-5-one, of melting point 180° C., were obtained.

20 parts of 3-methyl-5H-thiazolo[2,3-b]-quinazolin-5-one were dissolved in 150 parts of tetrahydrofuran at 50° C. and 34 parts of hydrobromic acid were added a little at a time. The reaction product was filtered off, washed with acetone and dried. 26.4 parts of the hydrobromide, of melting point 300°–305° C., were obtained.

Analysis: Calculated: Br 26.9. Found: Br 27.0.

Examples of thiazolo[2,3-b]-quinazolones of the formula I which may be used as active ingredients in the herbicides according to the invention include the following:

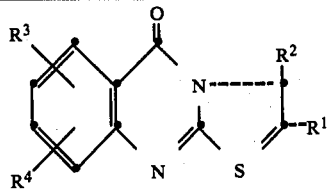

| Active ingredient no. | R$^1$ | R$^2$ | R$^3$ | R$^4$ | | M.p. [°C.] |
|---|---|---|---|---|---|---|
| 1 | H | CH$_3$ | H | H | | 180 |
| 2 | H | CH$_3$ | H | H | (perchlorate) | 310–315 |
| 3 | H | CH$_3$ | H | H | (sulfate) | 315–320 |
| 4 | CH$_3$ | CH$_3$ | H | H | | 175 |
| 5 | CH$_3$ | CH$_3$ | H | H | (hydrobromide) | 300–310 |
| 6 | Br | CH$_3$ | H | H | | 300–305 |
| 7 | H | H | H | H | | 144–146 |
| 8 | H | H | H | H | (hydrobromide) | 308–310 |
| 9 | COOC$_2$H$_5$ | CH$_3$ | H | H | | 130 |
| 10 | H | CH$_3$ | 7-CH$_3$ | H | | 180 |
| 11 | CH$_3$ | H | 8-CH$_3$ | H | | 165 |
| 12 | H | 4-chlorophenyl | 8-CH$_3$ | H | | 220 |
| 13 | CH$_2$Br | H | H | H | | 210 |
| 14 | CH$_3$ | H | 6-CH$_3$ | H | | 168 |
| 15 | CH$_3$ | H | H | H | | 183 |
| 16 | CH$_3$ | H | 7-CH$_3$ | H | | 200 |

The herbicides according to the invention are applied in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 7 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 8 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 4 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3 is intimately mixed with 97 parts by weight of particulate kaolin. A dust is obtained containing 3% by weight of the active ingredient.

VII. 30 parts by weight of compound no. 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal agents may be applied pre- or (preferably) postemergence. The agents may be applied before the unwanted plants have germinated from seed or sprouted from vegetative plant parts, or they may be applied to the leaves of unwanted and crop plants. Preferably, the novel active ingredients are applied after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year and the growth stage of the plants, and varies from 0.05 to 15 kg/ha and more, but is preferably from 0.125 to 5 kg/ha. The higher application rates are particularly suitable for total elimination of vegetation.

The herbicidal and growth-regulating action of herbicidal agents containing compounds of the formula I is demonstrated in greenhouse experiments.

The vessels employed were plastic flowerpots having a volume of 300 cm$^3$, and which were filled with a sandy loam containing about 1.5% humus. Peat was added to rice (grown for the post-emergence treatment) to ensure good growth. The seeds of the test plants were sown shallow, and separately, according to species. For the preemergence treatment, the active ingredients were applied to the surface of the soil immediately after the seeds had been sown. The compunds were emulsified or suspended in water as vehicle, and sprayed through finely distributing nozzles. The application rates may be about 2 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. The application rates for postemergence treatment varied from ingredient to ingredient, and were equivalent, for example, to 0.5, 1.0 and 3.0 kg of active ingredient per hectare.

The pots were set up in the greenhouse—species from warmer areas at from 20° to 35° C., and species from moderate climates at 15° to 25° C. The experiments were run for from 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants employed were *Abutilon theophrasti, Acanthospermum hispidum,* Amaranthus spp., *Arachis hypogaea, Avena sativa, Chenopodium album, Desmodium tortuosum, Euphorbia geniculata, Lamium purpureum, Mercurialis annua, Nicandra physaloides, Oryza sativa, Rumex obtusifolium, Sida spinosa, Solanum nigrum, Thlaspi arvense, Triticum aestivum, Veronica persica, Zea mays, Avena sativum, Daucus carota, Gossypium hirsutum, Hordeum vulgare,* and Setaria spp.

In investigations into selective herbicidal action on post-emergence application, herbicides according to the invention containing compounds nos. 1, 2, 3, 4, 6, 7 and 8 had a good herbicidal action. The application rates varied from 0.5 to 3.0 kg of active ingredient per hectare.

On preemergence application, for example compounds nos. 1, 2, 3, 6 and 7, applied at a rate of 2.0 kg/ha, combated unwanted plants without damaging cereal species.

In view of the good tolerance of the active ingredients and the many application methods possible, the compounds according to the invention, or agents containing them, may be used in a large number of crop plants, apart from those used in the greenhouse experiments, for removing unwanted plant growth.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arborum* *Gossypium herbaceum* *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |

| Botanical name | Common name |
|---|---|
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the agents according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the agents according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. To initiate the herbicidal action, wetting agents, spreader-stickers, and non-phytotoxic oils and oil concentrates may also be added.

We claim:

1. A process for combating unwanted plant growth which comprises: applying to the unwanted plants or their habitat a herbicidal composition comprising inert additives and, as a herbicidally active compound, an effective amount of a thiazolo-[2,3-b]-quinazolone of the formula

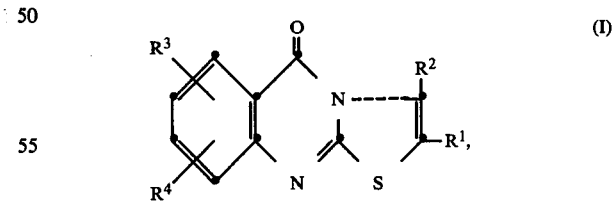

where
  $R^1$ and $R^2$ independently of one another are hydrogen, halogen, alkyl of 1-4 carbons or haloalkyl of 1-4 carbons, and
  $R^3$ and $R^4$ independently of one another are hydrogen or alkyl of 1-4 carbons, or an acid addition salt thereof.

2. A process as set forth in claim 1, wherein in the compound of formula I, $R^1$ is hydrogen, methyl, ethyl or bromomethyl, $R^2$ is hydrogen, methyl or ethyl, and $R^3$ and $R^4$, independently of one another, are hydrogen chloro or bromo, or an acid addition salt thereof.

3. A process as set forth in claim 1, wherein in the compound of formula I, $R^1$ is hydrogen, halogen or alkyl of 1 to 4 carbon atoms, $R^2$ is hydrogen or alkyl of 1 to 4 carbon atoms, and $R^3$ and $R^4$ are hydrogen or an acid addition salt thereof.

4. A process for combating unwanted plant growth which comprises: applying to the unwanted plants or their habitat a herbicidal composition comprising inert additives and, as a herbicidally active compound, an effective amount of a thiazolo-[2,3-b]-quinazolone of the formula

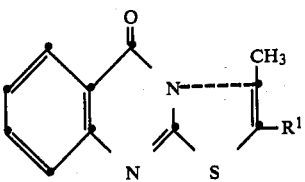

where $R^1$ is hydrogen or methyl, or an acid addition salt thereof.

* * * * *